United States Patent [19]

Cobb

[11] Patent Number: 5,034,562

[45] Date of Patent: Jul. 23, 1991

[54] ACID-SULFOLANCE CATALYZED PRODUCTION OF CYCLIC ALKYLATED COMPOUNDS

[75] Inventor: Raymond L. Cobb, Maretta, Ohio

[73] Assignee: Phillips Petroleum Company, Bartlesville, Okla.

[21] Appl. No.: 534,983

[22] Filed: Jun. 8, 1990

[51] Int. Cl.$^5$ .............................................. C07C 5/00
[52] U.S. Cl. ................................. 585/411; 585/452; 585/458
[58] Field of Search .................... 585/458, 411, 452

[56] References Cited

U.S. PATENT DOCUMENTS

| | | | |
|---|---|---|---|
| 4,440,966 | 4/1984 | Ferber et al. | 585/415 |
| 4,510,337 | 4/1985 | Cobb | 568/734 |
| 4,596,896 | 6/1986 | Cobb | 585/320 |

*Primary Examiner*—Curtis R. Davis
*Attorney, Agent, or Firm*—Archie L. Robbins

[57] ABSTRACT

An acid-sulfolane catalyzed process of preparing cyclic alkylated compounds such as indanes by reacting a monovinyl aromatic compound with an olefinic compound, such reaction further improved by the addition of a lanthanide oxide, or Group VI A elements and/or oxides or a mixture of such oxides.

19 Claims, No Drawings

ACID-SULFOLANE CATALYZED PRODUCTION OF CYCLIC ALKYLATED COMPOUNDS

BACKGROUND OF THE INVENTION

This invention relates to a new and useful process using various metal oxides in the acid-sulfolane catalyzed reactions of monovinyl aromatic compounds with olefinic compounds to produce cyclic alkylated compounds.

The acid catalyzed reaction of monovinyl aromatic compounds and olefinic compounds to produce cyclic alkylated compounds is known in the art. It is also known in the art that a primary drawback of these reactions is the dimerization of the starting reactants. The monovinyl aromatic compounds dimerize to produce both acyclic and cyclic dimers. The production of cyclic dimers is undesirable, because unlike the acyclic dimers they do not re-convert to the starting monovinyl aromatic compound. This, therefore, results in low yields of the desired cyclic alkylated products. Likewise, the starting olefinic compound dimerizes into a mixture of oligomers which do not necessarily re-convert to the starting olefinic compounds. This too results in low yields of the desired cyclic alkylated product.

Because of the aforementioned problems, it is of interest to the chemical industry to discover methods and/or reactants that minimize these undesired side reactions, while maximizing the yield of the desired product. This invention represents a successful attempt in maximizing the yield of the desired cyclic alkylated product.

SUMMARY OF THE INVENTION

It is an object of the invention to produce cyclic alkylated products in increased yields from the reaction of monovinyl aromatic compounds and olefinic compounds.

It is also an object of the invention to minimize the production of cyclic dimers while maximizing the production of acyclic dimers from reaction of monovinyl aromatic compounds and olefinic compounds.

It is also an object of the invention to produce cyclic alkylated products from a mixture of sulfolane-acid catalyzed reaction by the addition of a lanthanide, actinate, or rare earth oxide.

It is yet another object of the invention to produce cyclic alkylated products from a mixture of sulfolane-acid catalyzed reaction by the addition of a lanthanide oxide and/or an oxide of the Group VI A elements of the periodic element.

In accordance with this invention, a process is provided for the production of cyclic alkylated products by reacting at least one monovinyl aromatic compound and an olefinic compound in the presence of an acid-sulfolane catalyst. To this mixture of reactants and catalyst system is further added an effective amount of a lanthanide oxide, one or more Group VI A oxides, or a mixture of these oxides or elements of Group VI A of the periodic table of elements, for the purpose of facilitating cyclic alkylation reactions.

DETAILED DESCRIPTION OF THE INVENTION

The starting ingredients needed for this invention are monovinyl aromatic compounds, olefinic compounds, an acidic catalyst, sulfolane, and suitable metal oxides.

Monovinyl aromatic compounds which are useful in this invention can be represented by the general formulas:

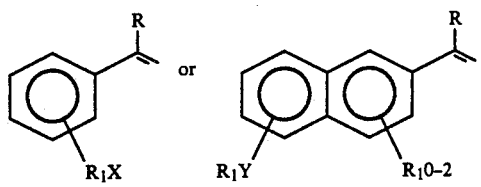

wherein $R_1$ is a $C_1$–$C_{10}$ carbon radical, a halide or an alkoxy derivative having the structure —OR, and X is 0–4; wherein R is H or a $C_1$–$C_{10}$ carbon radical and Y is 0–4 inclusive, with the proviso that at least one ortho position with respect to the vinyl substituent is not substituted. Examples of such monovinyl aromatic compounds are sytrene, alpha-methylstyrene (AMS), vinylnapthalene, 4-methyl-alpha-methylstyrene, and the like. Alpha-methylstyrene is the preferred member of this group. A molar ratio of about 1:0.05 to about 1:5 of these monovinyl aromatic compounds to olefinic compounds is generally useful. However, a ratio of about 1:0.2 up to about 1:3 is preferred.

Alternatively, also suitable as starting materials are precusors to monovinyl aromatic compounds represented by the general formula:

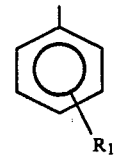

wherein $R_1$ can be ethyl, isopropyl, or a cyclohexyl group. With such compounds as starting materials, it is useful to use at a minimum a 1:2 molar ratio of the precursor aromatic compound to the olefinic compound. It is preferred that $R_1$ be an isopropyl group.

Suitable olefinic compounds are broadly contemplated to be organic compounds having at least one carbon-carbon double bond and any substituents which do not detrimentally interact with the catalyst employed for the alkylation reaction. Preferred olefinic compounds employed in the practice of the invention are mono-olefins. Those mono-olefins having from 4 up to about 30 carbon atoms with only one carbon-carbon double bond, and which are capable of forming tertiary carbocations under the alkylation process conditions are especially preferred, because the possibility of multiple alkylation reactions with consequent formation of a mixture of products is minimized.

The especially preferred group of olefinic compounds useful in the practice of this invention can also be described by the formula

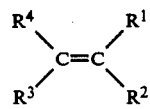

wherein each of $R^1$, $R^2$, $R^3$ and $R^4$ are independently selected from hydrogen and $C_1$ through $C_{10}$ alkyl or cycloalkyl radicals. In addition, $R^1$ and $R^2$ can be joined as part of a polymethylene radical or a halogen-, alkylor cycloalkyl-substituted polymethylene radical having about 2 to about 20 carbon atoms, i.e., a carbocyclic compound with an exocyclic double bond. Further, $R^1$ and $R^4$ can be similarly joined as part of a polymethylene radical or a halogen-, alkyl-, or cycloalkyl-substituted polymethylene radical having about 2 to about 20 carbon atoms, i.e., a carboxyxlic compound with an endocyclic double bond.

Examples of olefinic compounds useful in the practice of the invention include isobutylene, 2-methyl-1-butene, 2-methyl-2-butene, 2,3-dimethyl-2-butene, neohexene (tertiary-butylethylene), diisobutylene (2,4,4-trimethyl-1-pentene), 2-butene, 2-pentene, 1-methylcyclohexene, 1-methylcyclopentene, 2-hexene, and the like.

Examples of suitable acidic catalyst include but are not limited to sulfuric acid, acetic acid, and others disclosed in U.S. Pat. No. 4,596,896. The acidic catalyst is used in conjunction with sulfolane. The preferred acidic catalyst is sulfuric acid.

All lanthanide oxides are generally useful in this invention. However, cerium (IV) oxide is the preferred member of this group.

Likewise all Group VI A elements and/or oxides of the periodic table of elements are also useful in this invention. However, tungstate and molybdate or their oxides are preferred.

There are, in general, at least, three separate embodiments of this invention. In the first embodiment, a lanthanide oxide such as cerium IV oxide is added to the reactants catalyzed by an acid-sulfolane catalyst system. In the second embodiment, a Group VI A element such as tungstate and/or molybdate is added to the starting reactants catalyzed by an acid-sulfolane catalyst system. And in the third embodiment of this invention, a lanthanide oxide such as cerium (IV) oxide plus one or more Group VI A element or oxide such as tungsten or molybdenum oxide is added to the starting reactants catalyzed by an acid-sulfolane catalyst system. In all of these embodiments, the preferred acidic catalyst is sulfuric acid.

These various embodiments, however, use the same process, reaction conditions, and quantities of ingredients. For the sulfuric acid, while a concentration of up to 96% is useful, a 75-80% concentration is preferred. Likewise, although the reactions can be carried out at temperatures ranging from about 10° C. to about 70° C., a temperature range of about 20° to about 40° C. is preferred. A molar ratio of 1.4:1 of the olefinic compound to the monovinyl aromatic compound is the most distinctly preferred ratio of starting reactants.

This invention does not necessarily require large volumes of the acid-sulfolane catalyst system. It is, however, preferred that a 40 volume percent, based on total hydrocarbon feed (AMS+2MB-2), of both the acid and sulfolane be used. The use of various reaction media such as cyclohexane, toluene, dichloromethane and the like is explicitly disfavored for this invention. Likewise disfavored, is the use of surface active agents such as polyethoxylated tert-dodecylsulfinate and the like.

Any device and/or method suitable for the mixing of chemical ingredients is useful for carrying this invention. With the aid of such devices or methods, this invention in its most simplistic form consists of the following steps: Preparing the acid-sulfolane catalyst system in a suitable vessel; adding an effective amount of the lanthanide oxide, or Group VI A oxide(s), or mixtures thereof; followed by adding the monovinyl aromatic compound and olefinic compound to the vessel containing the catalyst system and oxide(s); and maintaining the reaction mixture at a temperature of from about 10° C. to about 70° C.

The completion of this reaction yields a cyclic alkylated product. In one specific embodiment of this invention reacting α-methylstyrene (AMS) and 2-methyl-2-butene (2MB-2) gave good yields of 1,1,2,3,3-pentamethylidane (isoPMI). In general, though, the desired cyclic alkylated product is prepared by selecting a suitable monovinyl aromatic compound as the starting reactant.

The following illustrative examples further detail the various aspects of this invention.

EXAMPLE I

Cyclialkylation of α-methylstyrene (AMS) with Olefins Catalyzed by Phosphoric Acid To a 500 ml Erlenmeyer flask containing 20 ml of phosphoric acid having various concentrations shown in Table 1, 30 ml of α-methylstyrene (AMS) and 30 ml of 2-methyl-2-butene (2MB2) were slowly added in 5-7 minutes while stirring. The flask was heated in a water bath to desired temperatures as indicated in Table 1.

Samples of the reaction mixture were periodically removed from the flask after the reaction started. The samples were analyzed for 1,1,2,3,3-pentamethylindane (PMI) on a Hewlett Packard (HP) 5880 gas chromotograph using a 50 meter capillary column, having oven temperature set at 50° C. for 8 minutes and programmed at 10° C./minute to 265° C. The results are shown in Table 1. It should be noted that in order to achieve satisfactory reproducibility, the testing samples made from the reaction mixture should be prepared in the same manner. The final product, obtained after the reaction was completed, was washed 2-3 times with water to remove the catalyst followed by distillation in in vacuo.

TABLE 1

| Cyclialkylation of AMS with 2MB2 to PMI | | | | |
|---|---|---|---|---|
| Run | Catalyst[a] | Temp (°C.) | Conv. (%)[b] | Selectivity (%) |
| 1 | 80% $H_3PO_4$ + toluene | 40 | 68 | 50.3 |
| 2 | 85% $H_3PO_4$ + toluene | 40 | 74 | 54.8 |
| 3 | 89% $H_3PO_4$ + toluene | 40 | 47 | 54.5 |
| 4 | 100% $H_3PO_4$ | 50 | 100 | 40.8 |
| 5 | 85% $H_3PO_4$ + acetic acid | 45 | 47 | —[c] |
| 6 | 100% $H_3PO_4$ + toluene | 25 | 30 | 57.3 |
| 7 | 100% $H_3PO_4$ + heptane | 28 | 85 | 14.5 |
| 8 | 89% $H_3PO_4$ | 28 | 100 | 34.6 |
| 9 | 89% $H_3PO_4$ + sulfolane | 28 | 100 | 9.0 |
| 10 | 69% $H_3PO_4$ | 50 | 100 | 37.0 |
| 11 | 69% $H_3PO_4$ + sulfolane | 50 | 100 | 54.0 |
| 12 | 69% $H_3PO_4$ | 70 | 100 | 36.7 |
| 13 | 69% $H_3PO_4$ + sulfolane | 70 | 100 | 51.0 |
| 14 | 63% $H_3PO_4$ | 50 | 100 | 37.7 |
| 15 | 63% $H_3PO_4$ + sulfolane | 50 | 100 | 51.7 |
| 16 | 57% $H_3PO_4$ | 50 | 100 | 32.7 |
| 17 | 57% $H_3PO_4$ + sulfolane | 50 | 100 | 48.4 |

[a] The catalyst comprised 20 ml of the indicated $H_3PO_4$ and 15 ml of a medium, if present.
[b] The conversion was calculated based on AMS after the reaction was started for 8 hours, and was determined by GC.
[c] Little or no PMI was detected.

The results shown in Table 1 demonstrate that a low phosphoric acid concentration worked as well as 100% $H_3PO_4$ (Runs 4, 10, and 14); that the optimal temperature appeared to be around 50° C. for the best selectivity and conversion (Runs 10-13); and that presence of a medium tended to improve the conversion and/or selectivity (Runs 4 and 6-17). Among the solvents tested, acetic acid and heptane resulted in very poor selectivity (Runs 5 and 7) toluene tended to improve the selectivity (Runs 1-4 and 6), and sulfolane showed improvement in both conversion and selectivity (Runs 10-17), with the exception of Runs 8 and 9. It is concluded that the presence of sulfolane as a medium improves both catalytic activity and selectivity.

EXAMPLE II

The runs summarized in Table 2 were carried out using the same procedure as the runs of Example I except that 100% $H_3PO_4$ was used and sulfolane was present in the catalyst mixture in volume ratios indicated in Table 2.

TABLE 2

Cyclialkylation of AMS and 2MB2 with 100% $H_3PO_4$ in Sulfolane Medium

| Run | Volume (%)[a] $H_3PO_4$ | Sulfolane | Temp (°C.) | Conversion (%)[b] | Selectivity (%)[c] |
|---|---|---|---|---|---|
| 18 | 80 | 40 | 33 | 100 | 50.1 |
| 19 | 80 | 40 | 50 | 100 | 47.2 |
| 20 | 40 | 40 | 35 | 100 | 49.1 |
| 21 | 40 | 40 | 50 | 100 | 54.0 |
| 22 | 40 | 80 | 50 | 100 | 30.2 |
| 23 | 40 | 20 | 50 | 100 | 45.8 |
| 24 | 40 | 0 | 50 | 100 | 37.1 |

[a]Based on total hydrocarbon feed (AMS + 2MB2).
[b]Reaction time was 8 hours.
[c]Based on PMI.

The results shown in Table 2 demonstrate that optimal $H_3PO_4$: sulfolane volume ratio is about 1:1 by volume. In other words, using substantially equal amounts of acid and sulfolane appear to give best results.

EXAMPLE III

Cyclialkylation of AMS and 2MB2 using $H_2SO_4$ as Catalyst

The runs summarized in Table 3 were carried out using the same procedure as the runs of Example II with the exception that sulfuric acid was used as catalyst. The results are shown in Table 3.

TABLE 3

Cyclialkylation of AMS and 2MB2 to PMI

| Run | $H_2SO_4$[a] | Sulfolane[b] | Temp (°C.) | Conv. (%)[c] | Selectivity (%)[d] |
|---|---|---|---|---|---|
| 25 | 80 | — | 25 | 100 | 39.3 |
| 26 | 80 | + | 25 | 100 | 54.4 |
| 27 | 75 | — | 25 | 90 | 48.6 |
| 28 | 75 | + | 25 | 95 | 62.2 |
| 29 | 72 | — | 25 | 90 | 46.5 |
| 30 | 72 | + | 25 | 95 | 55.6 |

[a]The sulfuric acid shown was 40% (v/v) as of total volume of hydrocarbon feed; concentrated sulfuric acid was used.
[b]Sulfolane, if present, was also 40% of total volume of hydrocarbon feed.
[c]Conversion was based on AMS and was measured at 8 hours after reaction started.
[d]Selectivity was based on PMI.

The results show that, in the presence of sulfolane, the reaction can be run at lower temperatures when sulfuric acid is used than when phosphoric acid is used as catalyst. Table 3 also shows that about 75% $H_2SO_4$ was probably the best concentration for high selectivity (Run 28). The selectivity dropped somewhat when the concentration was increased to 80% or decreased to 72%. Finally, Table 3 demonstrates that 25° C. was not an optimal temperature for catalytic activity, in terms of conversion.

Additional runs were carried out to determine the optimal temperature for sulfuric acid-catalyzed cyclialkylation. This is shown in Table 4.

TABLE 4

Temperature Effect on $H_2SO_4$ Catalyzed Cyclialkylation

| Run | Temp (°C.) | Conversion (%)[b] | Selectivity (%)[c] |
|---|---|---|---|
| 31 | 25 | 90 | 48.6 |
| 32 | 30 | 100 | 52.0 |
| 33 | 40 | 100 | 56.8 |
| 34 | 42 | 100 | 55.6 |

[a]Catalyst employed was 75% $H_3PO_4$ in sulfolane each was 40% (v/v) of total hydrocarbon feed. The measurements were done at 8 hours after reaction started.
[b]Based on AMS.
[c]Based on PMI.

The results shown in Table 4 indicated that the preferred temperature for sulfuric acid-sulfolane catalyzed cyclialkylation is about 40° C.

EXAMPLE IV

Effect of Cerium (IV) Oxide and Other Additives on Cyclialkylation

The runs summarized in Table 5 were carried out using the same procedure as the runs of Example III except that $CeO_2$ and/or other metal salts were present in the catalyst medium. The results are shown in Table 5.

TABLE 5

Effect of $CeO_2$ and/or Other Metal Salts on Cyclialkylation[a]

| Run | Additive[b] $CeO_2$ | $Na_2MoO_4$ | $Na_2WO_4$ | Selectivity (%)[c] |
|---|---|---|---|---|
| 35 | — | — | — | 60.5 |
| 36 | 1.0 | — | — | 66.0 |
| 37 | — | — | 0.5 | 68.1 |
| 38 | — | 0.5 | — | 69.0 |
| 39 | 1.0 | 0.5 | — | 67.0 |
| 40 | 1.0 | 0.5 | 0.5 | 69.0 |

[a]Catalyst used was the same as in Example III (Table 4) except that additives shown were included. The reaction was carried out at 40° C. and 100% conversion was reached in less than 2 hours.
[b]The quantities shown are in grams.
[c]Based on PMI and was calculated at 65% conversion.

Table 5 clearly demonstrates that, in the presence of the additive(s), catalytic activity was improved (see footnote a) because each reaction was completed in less than 2 hours and the selectivity was improved by about 10-15%.

While this invention has been described in detail for the purpose of illustration, it is not to be construed as limited thereby but is intended to cover all changes and modifications within the spirit and scope thereof.

That which is claimed is:

1. A process for preparing cyclic alkylated products comprising reacting a monovinyl aromatic compound with an olefinic compound in the presence of an acid-sulfolane catalyzed system, and at least one compound selected from the group consisting of lanthanide oxides, Group VI A elements and Group VI oxides, at a temperature of from about 10° C. to about 70° C.

2. A process in accordance with claim 1 wherein said produced cyclic alkylated product is 1,1,2,3,3-pentamethylindane.

3. A process in accordance with claim 1 wherein said monovinyl aromatic compound is represented by the general formulas:

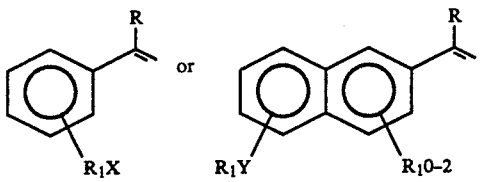

wherein $R^1$ is a $C_1-C_{10}$ carbon radical, a halide or an alkoxy derivative having the structure —OR, and X is 0–4; wherein R is H or a $C_1-C_{10}$ carbon radical and Y is 0–4 inclusive, with the proviso that at least one ortho position with respect to the vinyl substituent is not substituted.

4. A process in accordance with claim 1 wherein said monovinyl aromatic compound is synthesized from at least one precusor compound represented by the general formula:

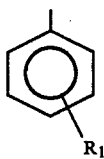

wherein $R_1$ is ethyl, isopropyl, or a cyclohexyl group.

5. A process in accordance with claim 1 wherein said monovinyl aromatic compound is selected from the group consisting of styrene, alpha-methylstyrene, vinyl napthalene and 4-methyl-alpha-methylstyrene.

6. A process in accordance with claim 1 wherein said monovinyl aromatic compound is alpha-methylstyrene.

7. A process in accordance with claim 1 wherein said olefinic compound is represented by the general formula:

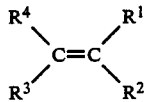

wherein each of $R^1-R^4$ is independently selected from H and $C_1-C_{10}$ alkyl or cycloalkyl radical; or $R^1$ and $R^2$ or $R^4$ can be joined as part of a polymethylene or alkyl- or cycloalkyl-substituted polymethylene radical having two to twenty carbon atoms.

8. A process in accordance with claim 1 wherein said olefinic compound is selected from the group consisting of 2-methyl-1-butene, 2-methyl-2-butene, 2,3-dimethyl-1-butene, 3-methyl-1-butene, neohexene, isobutylene, and diisobutylene.

9. A process in accordance with claim 1 wherein said olefinic compound is 2-methyl-2-butene.

10. A process in accordance with claim 1 wherein said lanthanide oxide is cerium (IV) oxide.

11. A process in accordance with claim 1 wherein said Group VI A oxide is selected from the group consisting of tungsten and molybdum oxides.

12. A process in accordance with claim 1 wherein said monovinyl aromatic compound is reacted with said olefinic compound in a 1:1.4 molar ratio.

13. A process in accordance with claim 1 wherein said acid is sulfuric acid.

14. A process in accordance with claim 13 wherein said sulfuric acid concentration is from about 75% to about 80%.

15. A process in claim 1 wherein substantially equal volumes of the acid and sulfolane comprise the acid-sulfolane catalyst system.

16. A process for preparing 1,1,2,3,3-pentamethylidane comprising:
(a) combining alpha-methylstyrene with 2-methyl-2-butene in about a 1:1.4 molar ratio respectively of reactants in the presence of an oxide selected from the group consisting of tungsten oxide, molybdenum oxide, cerium (IV) oxide, and mixtures thereof and a catalyst system comprising a substantially equal volume mixture of about 75% concentration sulfuric acid and sulfolane and
(b) maintaining the reaction mixture at a temperature of from about 20° C. to 40° C.

17. A process as in claim 16 wherein said oxide is cerium (IV) oxide.

18. A process as in claim 16 wherein said oxide is selected from the group consisting of tungsten and molybdenum oxides.

19. A process as in claim 16 wherein said oxide consists of cerium (IV) oxide, tungsten oxide, and molybdenum oxide.

* * * * *